United States Patent [19]

Ashe et al.

[11] Patent Number: 5,602,755

[45] Date of Patent: Feb. 11, 1997

[54] METHOD FOR PREDICTING CHEMICAL OR PHYSICAL PROPERTIES OF COMPLEX MIXTURES

[75] Inventors: Terrence R. Ashe, Point Edward; Jeffrey D. Kelly; Tian C. Lau, both of Scarborough; Ronald T.-K. Pho, Richmond Hill, all of Canada

[73] Assignee: Exxon Research and Engineering Company, Florham Park, N.J.

[21] Appl. No.: 494,201

[22] Filed: Jun. 23, 1995

[51] Int. Cl.⁶ .................................................. G06F 17/00
[52] U.S. Cl. ................................... 364/498; 364/499
[58] Field of Search ...................................... 364/498, 497, 364/499, 571.01, 571.02, 571.04; 73/1 R, 23.35–23.42; 250/281, 288, 339.12, 339.13, 252.1

[56] References Cited

U.S. PATENT DOCUMENTS

| | | | |
|---|---|---|---|
| 3,898,837 | 8/1975 | Boege | 73/23.1 |
| 4,353,242 | 10/1982 | Harris et al. | 73/23.1 |
| 4,583,183 | 4/1986 | Winiecki et al. | 364/498 |
| 4,807,148 | 2/1989 | Lacey | 364/498 |
| 4,835,708 | 5/1989 | Frans | 364/497 |
| 4,916,645 | 4/1990 | Wuest et al. | 364/571.04 |
| 5,119,315 | 6/1992 | Kemp et al. | 364/498 |
| 5,121,337 | 6/1992 | Brown | 364/498 |

FOREIGN PATENT DOCUMENTS 3-100463  4/1991  Japan ............................... 33/22

*Primary Examiner*—James P. Trammell
*Attorney, Agent, or Firm*—James H. Takemoto

[57] ABSTRACT

A Method for predicting the properties of a complex hydrocarbon mixture which comprises selecting one or more known chemical, perceptual, physical or performance properties of the complex mixture and creating a training set from reference samples which contain characteristic molecular species present in the mixture. The reference samples are subjected to GC/MS analysis wherein the often collinear data generated are treated by multivariate correlation methods. The training set produces coefficients which are multiplied by the matrix generated from a GC/MS analysis of an unknown mixture to produce a predicted value for the chemical, performance or physical property or groups of properties selected.

10 Claims, 1 Drawing Sheet

FLOW DIAGRAM FOR PREDICTING PROPERTIES OF HYDROCARBON MIXTURES

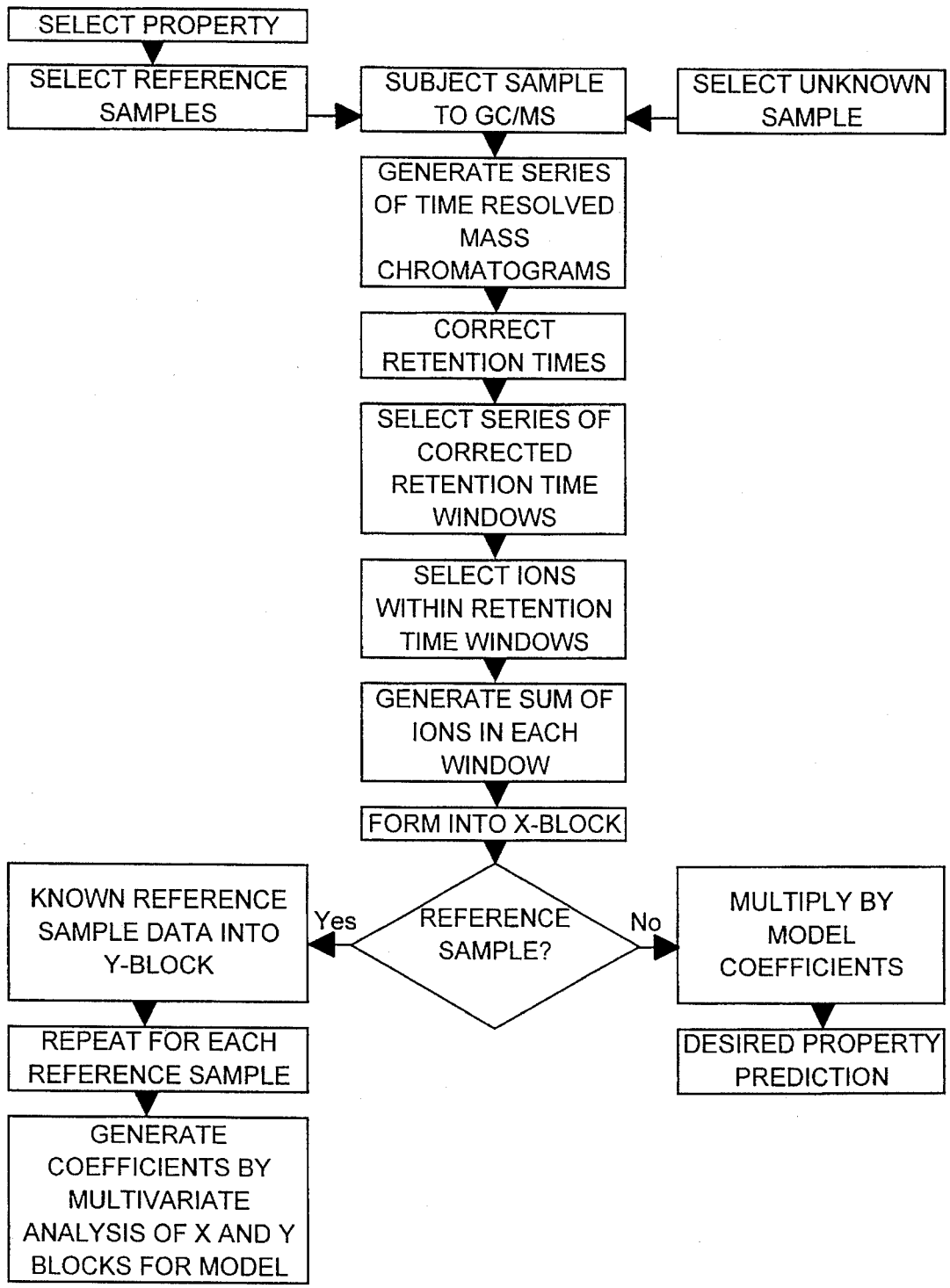
FLOW DIAGRAM FOR PREDICTING PROPERTIES OF HYDROCARBON MIXTURES

METHOD FOR PREDICTING CHEMICAL OR PHYSICAL PROPERTIES OF COMPLEX MIXTURES

BACKGROUND OF THE INVENTION

1. Field Of The Invention

This invention relates to a method for rapidly predicting the physical and chemical properties of a complex hydrocarbon mixture using a combination of gas chromatography and mass spectrometry.

2. Description Of The Related Art

Traditional wet chemistry methods for obtaining physical and chemical properties of a complex hydrocarbon mixture are very time consuming. Hydrocarbon mixtures typically contain many thousands of different chemical compounds so only bulk properties for classes of compounds are usually measured, e.g., distillation range, viscosity, pour point and the like.

Gas chromatography has been used to predict physical and performance properties of hydrocarbon mixtures boiling in the gasoline range. Crawford and Hellmuth, Fuel, 1990, 69, 443–447, describe the use of gas chromatography and principal components regression analysis to predict the octane values for gasolines blended from different refinery streams. Japanese laid-open patent application JP 03-100463 relates to a method of estimating the cetane number for fuel oils by separating an oil sample into its components using gas chromatograpy, measuring the signal strength of ion intensities at characteristic masses in the mass spectrum, and correlating these ion intensities to cetane number using multiple regression analysis.

Combined gas chromatography/mass spectrometry (GC/MS) analysis has been done on crude oils. U.S. Pat. No. 5,119,315 discloses a method for aligning sample data such as a mass chromatogram with reference data from a known substance. Williams et al, 12th European Assoc. Organic Geochem., Organic Geochem. Int. Mtg. (Germany 09/16-20/85); Organic Geochemistry 1986, Vol. 10 (1–3) 451–461, discusses the biodegradation of crude oils as measured by GC/MS analysis.

It would be desirable to have a method for predicting properties of complex hydrocarbon mixtures using gas chromatography/mass spectrometry which method involves analyzing collinear data.

SUMMARY OF THE INVENTION

This invention relates to a method for predicting physical, performance, perceptual or chemical properties of a complex hydrocarbon mixture which comprises:

(a) selecting at least one property of the hydrocarbon mixture;

(b) selecting reference samples, said reference samples containing characteristic compound types present in the complex mixture and which have known values for the property or properties selected in step (a);

(c) producing a training set by the steps of:
  (1) injecting each reference sample into a gas chromatograph which is interfaced to a mass spectrometer thereby causing at least a partial separation of the hydrocarbon mixture into constituent chemical components;
  (2) introducing the constituent chemical components of each reference sample into the mass spectrometer, under dynamic flow conditions;
  (3) obtaining for each reference sample a series of time resolved mass chromatograms;
  (4) calibrating the mass chromatograms to correct retention times;
  (5) selecting a series of corrected retention time windows;
  (6) selecting within each retention time window a series of molecular and/or fragment ions, said ions being representative of characteristic compounds or compound classes expected within the retention time window;
  (7) recording the total amount of each characteristic compound or compound group selected in step c(6);
  (8) forming the data from steps c(6) and c(7) into a X-block matrix;
  (9) forming the data selected in (a) for reference samples selected in (b) into a Y-block matrix;
  (10) analyzing the data from steps c(8) and c(9) by multivariate correlation techniques including Partial Least Squares, Principal Component Regression or Ridge Regression to produce a series of coefficients;

(d) subjecting an unknown hydrocarbon mixture to steps c(1) and c(3) in the same manner as the reference sample to produce a series of time resolved mass chromatograms;

(e) repeating steps c(4) to c(8) for each mass chromatogram from step (d);

(f) multiplying the matrix from step (e) by the coefficients from step c(10) to produce a predicted value of the property or properties.

The gas chromatography/mass spectrometry (GC/MS) method described above can be used to rapidly predict a wide range of chemical, perceptual, performance and/or physical properties of complex hydrocarbon mixtures such as chemical composition and concentration data on specific components, distillation properties, viscosity, pour point, cloud point, flash point, octane number, cetane number, viscosity index, color, odor and the like in a short time period.

BRIEF DESCRIPTION OF THE DRAWING

FIG. 1 is a schematic flow diagram showing the method for predicting physical, performance, perceptual or chemical properties of a complex hydrocarbon mixture.

DETAILED DESCRIPTION OF THE INVENTION

The present method for predicting chemical, perceptual, performance and physical properties for complex hydrocarbon mixtures involves quantitative identification of components using a combination of retention times from a GC analysis coupled with target fragment and/or molecular ions produced by the MS. The MS information is compared to a set of known properties from reference samples which form a training set. By mathematically comparing the experimental data with that of the training set, one may predict the desired properties of the unknown mixture. The method is illustrated schematically in FIG. 1.

GC/MS utilizes a gas chromatograph interfaced with a mass spectrometer. While a chromatographic method such as supercritical fluid chromatography, liquid chromatography or size exclusion chromatography may be used to separate the mixture into components or mixtures of components, gas chromatography, especially capillary gas chromatography is preferred for interfacing with a mass spectrometer. Both GC and MS utilize computer software for instrument control, data acquisition and data reduction. The computer platform should be capable of acquiring at least 2000 mass spectra in about 7 minutes.

The sample mixture to be analyzed is first injected into a GC where the mixture components are separated as a function of retention time, typically on the basis of boiling point. Only partial chromatographic resolution of mixture components is necessary. The GC oven temperature control is usually programmed for samples with a wide boiling range. Separated components may also be identified by a detector such as a flame ionization detector, thermal conductivity detector, atomic emission detector or electron capture detector.

The separated or partially separated components are then transferred to the mass spectrometer under dynamic flow conditions. Since a GC operates under atmospheric pressure and a MS under vacuum conditions (about $10^{-3}$ kPa), the instrument interface requires a coupling device such as a molecular separator (e.g., jet, membrane, etc.), open split coupler or capillary direct interface to efficiently transfer sample while minimizing carrier gas effects.

Depending on the nature of the sample, the mixture may be introduced directly into a MS using a direct insertion probe without a prior GC separation step. Other thermal separation techniques not involving a GC may be used to introduce the sample into the mass spectrometer.

In the MS, sample molecules are bombarded with high energy electrons thereby creating molecular ions which fragment in a pattern characteristic of the molecular species involved. A continuous series of mass spectra are obtained over a scan range of at least 10 to at least 450 daltons. The mass spectral data may also be acquired under selected ion monitoring (SIM) mode. In the selected ion mode, care must be taken to select ions representative of the components of interest and to operate under repeatable conditions. A variety of MS instruments may be used including low resolution, high resolution MS/MS (hybrid or triple quadrupole, etc.) ion cyclotron resonance and time of flight. Any ionization technique may be used, such as electron ionization, chemical ionization, multiphoton ionization, field desorption, field ionization, etc., provided that the technique provides either molecular or fragment ions which are suitable for use in the analysis procedure.

The results of sample analysis are a series of l mass spectra. The mass spectra are divided into n time intervals where n is an integer from 1 to l. At least one diagnostic ion is chosen from each of m time intervals where m is an integer from 1 to n. The term "diagnostic ion" refers to an ion which is representative a compound, a chemical class, or a perceptual, performance or physical property correlated thereto. Regardless of whether mass spectral data are obtained in the scan or selected ion monitoring mode, it is important that they be obtained under conditions which yield diagnostic ions of suitable and repeatable intensity and accuracy.

If the mass spectral data are acquired in the scan mode, the mass range covered during the acquisition should be sufficient to provide acquisition of all of the ions which could be used as diagnostic ions during mathematical treatment of each mass spectral scan. If the mass spectral data are acquired in the selected ion monitoring mode, then care must be taken that the ions selected for monitoring are suitable for use in measuring the components of interest.

The sample mass spectral data are then compared to mass spectral data from a series of reference samples with known physical, performance, perceptual or chemical properties. In order to compare reference mass spectral data with sample mass spectral data, it may be desirable to time align the sample data to help ensure the integrity of the comparison. There are commercially available computer programs for such data alignment, for example, Hewlett-Packard GC/MS software G 1034C version C.01.05.

The reference mass spectral data, and associated properties data, are arranged in matrix form for mathematical treatment as described below. In the case of chemical composition information, one matrix is formed of reference sample ion intensities at given masses and the other matrix contains known ion intensities for molecular fragment ions of known components. The training set for chemical composition data is thus made up of mass spectral data for different components characteristic of components expected to be found in the sample mixtures. Similar training sets can be formed for other chemical or perceptual or performance or physical properties of interest. These training sets form one block or matrix of data (Y-block or properties matrix). The actual sample mass spectral data (which may have been time aligned) form the other block (X-block) or matrix of data. These two matrices are subjected to mathematical treatments known as Partial Least Squares (PLS), or Principal Component Regression (PCR), or Ridge Regression (RR) to obtain a mathematically describable relationship between the properties data and mass spectral data, known as a model. Coefficients provided by this model are mathematically combined with the suitably treated mass spectral data from samples with unknown desired properties to:

a) predict desired properties;

b) assess the suitability of the model for such predictions, and c) diagnose the stability and general correctness of the process that yielded the mass spectral data.

PLS/PCR/RR are described in the literature, e.g., Wold S., A. Ruhe, H. Wold, and W. J. Dunn, "The Collinearity Problem in Linear Regression. The Partial Least Squares (PLS) Approach to Generalized Inverses", SIAM J. Sci. Stat. Comput., 1984 5(3), 735–743, or Geladi P., and B. R. Kowalki, "Partial Least Squares Regression: A Tutorial", Anal. Chim. Acta, 1986, 185, 1–17, or Hökuldsson A., "PLS Regression Methods", J. Chemometrics, 1988, 2, 211–228, or in many other articles in journals such as the Journal of Chemometrics or Intelligent Laboratory Systems; Frank, I. and J. Friedman, "A Statistical View Of Some Chemometrics Regression Tools", Technometrics, 1993, Vol. 35, No. 2; Jackson, J. E., "A User's Guide To Principal Components", Wiley-Interscience, New York, 1991; Montgomery, D.C., "Introduction To Linear Regression Analysis", Wiley-Interscience, New York, 1990; and Martens, H., and T. Naes, "Multivariable Calibration", Wiley-Interscience, New York, 1989.

When dealing with a complex mixture, it is necessary to select appropriate masses or groups of masses at specific retention times for a particular compound or classes of compounds. The selection of such masses are the basis for a set of rules which then forms the data for the training set. There are no set procedures for such a selection process. The researcher must select appropriate masses for compounds of interest. For example, paraffinic hydrocarbons yield fragment ions at masses 43, 57, 71, 85, . . . daltons, and these masses may be used as diagnostic of this class of compounds. Moreover, when coupled with retention time data, it is possible to identify concentrations of specific compounds within this class of compounds. In a similar manner, training sets for other chemical, perceptual, performance or physical properties may be developed by correlating compositional data with other properties of interest, e.g., boiling range, viscosity and the like. The result of a mathematical treatment such as PLS/PCR/RR of the training set is a set of coefficients for the properties of interest.

These coefficients are then multiplied by the data matrix for the sample. The result is a prediction of the desired property or properties. The method of the invention is further illustrated by the following examples.

EXAMPLE 1

The method for predicting the performance properties of a complex hydrocarbon mixture is demonstrated in this example using cetane number as the specific property for purposes of illustration. The method is generally applicable to a range of other performance properties as well as physical, perceptual or chemical properties of such mixtures.

The initial consideration is to establish a set of standard GC/MS operating parameters so that the GC/MS analytical data used for predicting properties are obtained under the same operating conditions. The GC/MS instrument used in this example is a Hewlett-Packard 5972 Mass Selective Detector interfaced to a Hewlett-Packard 5890 Series II Gas Chromatograph fitted for use with microbore columns.

The GC/MS operating conditions are summarized in Table 1.

TABLE 1

| GC CONDITIONS | |
|---|---|
| Column | Phenyl Silicone (such as HP-5) 10 m × 0.1 mm, 17 micron film thickness |
| Temperature Program | |
| Initial Temperature (°C.) | 35 |
| Initial Time (minutes) | 2 |
| Program Rate (°C./minute) | 30 |
| Final Temperature (°C.) | 275 |
| Final Time (minutes) | 5 |
| Carrier Gas | Helium |
| Linear Velocity | 25.6 |
| Injection Volume μL | 0.5 |
| Split Ratio | 500:1 |
| Column Head Pressure, kPa | Approximately 260 |
| Interface Temperature (°C.) | 295 |
| MASS SPECTROMETER CONDITIONS | |
| Ionization Mode | Electron Ionization, 70 eV nominal |
| Mass Range Scanned (daltons) | 15–450 |
| Cycle Time (minutes) | 0.003 |

In order to predict properties of an unknown hydrocarbon mixture, it is first necessary to select reference samples having known values of the property or properties of interest. These reference samples are used to form a training set as described below. Fourteen different diesel fuel blends were prepared from five typical refinery streams used for blending diesel fuels. These refinery streams are designed as HAGO/KGO (Heavy Atmospheric Gas Oil/Coker Gas Oil), HCISDIST (Hydrocracker Distillate), LOPOUR (Low Pour Point Distillate), CLHO (Cat Light Heating Oil) and SRLGO (Straight Run Light Gas Oil), and the liquid volume percent of the blends as well as the cetane numbers as determined by ASTM 613-86 are shown in Table 2.

TABLE 2

| SAMPLE | CETANE NUMBER* | HAGO/KGO (VOL %) | HCISDIST (VOL %) | LOPOUR (VOL %) | CLHO (VOL %) | SRLGO (VOL %) |
|---|---|---|---|---|---|---|
| A | 32.6 | 24.75 | 8.75 | 24.25 | 42.25 | 0.00 |
| B | 33.5 | 26.25 | 9.25 | 25.75 | 38.75 | 0.00 |
| C | 34.1 | 27.25 | 9.75 | 27.25 | 35.25 | 0.00 |
| D | 35.0 | 29.25 | 10.25 | 28.50 | 32.00 | 0.00 |
| E | 36.3 | 30.75 | 10.75 | 30.00 | 28.50 | 0.00 |
| F | 37.4 | 32.00 | 11.25 | 31.50 | 25.25 | 0.00 |
| G | 38.5 | 33.50 | 11.75 | 33.00 | 21.75 | 0.00 |
| H | 39.2 | 35.00 | 12.25 | 34.25 | 18.50 | 0.00 |
| I | 40.0 | 36.50 | 12.75 | 35.75 | 15.00 | 0.00 |
| J | 41.0 | 38.00 | 13.25 | 37.25 | 11.50 | 0.00 |
| K | 42.0 | 39.25 | 13.75 | 38.75 | 8.25 | 0.00 |
| L | 43.2 | 40.75 | 14.50 | 40.00 | 4.75 | 0.00 |
| M | 43.9 | 42.25 | 15.00 | 41.50 | 1.25 | 0.00 |
| N | 45.3 | 40.25 | 14.25 | 39.50 | 0.00 | 6.00 |
| HAGO | 44.9 | | | | | |
| HCISDIST | 43.8 | | | | | |
| LOPOUR | 44.1 | | | | | |
| CLHO | 15.0 | | | | | |
| SRLGO | 54.7 | | | | | |

*as measured by ASTM D 613-86

A data treatment method should be selected prior to obtaining raw GC/MS data. Two types of data treatments which may be used are Chemist's Rules and Hydrocarbon Compound Type Analysis as described, for example, in ASTM D2425-86.

Chemist's Rules involve two separate sections: (1) a calibration section to correct retention times, i.e., the time between zero and the time when a given peak occurs; and (2) the actual Rules which are based on a selected series of masses corresponding to prominent compounds or compound types expected in the type of hydrocarbon mixture under investigation. These compounds or compound types are selected on the basis that they have prominent molecular and/or fragment ions unique to that compound or molecular series. A portion of the Chemist's Rules are shown in Table 3. The full set of Chemist's Rules for Distillates is shown as a table following Example 4.

TABLE 3

| RULES (a) | COMPOUND (b) | Mass (c) | | | | | | RETENTION TIME (d) START | END |
|---|---|---|---|---|---|---|---|---|---|
| 1 | Paraffins | 43 | 57 | 71 | 85 | 99 | 113 | 0.400 | 3.162 |
| 2 | Cycloparaffins | 41 | 55 | 69 | 83 | 97 | 111 | 0.400 | 3.162 |
| 3 | Toluene | 91 | 92 | | | | | 0.400 | 2.860 |
| 4 | $C_nH_{2n-8}$ | 117 | 131 | 145 | 159 | 163 | 177 | 2.851 | 3.162 |
| 5 | $C_nH_{2n-6}$ | 91 | 105 | 119 | 133 | 147 | 161 | 2.851 | 3.162 |
| 6 | $C_nH_{2n-12}$ | 141 | 155 | 169 | 183 | 197 | 211 | 2.851 | 3.162 |
| 7 | $C_nH_{2n-10}$ | 115 | 129 | 143 | 157 | 171 | 185 | 2.851 | 3.162 |
| 8 | $C_nH_{2n-18}$ | 178 | 191 | 205 | 219 | 233 | 247 | 2.851 | 3.162 |
| 9 | n-C8 | 43 | 57 | 71 | 85 | 99 | 114 | 3.162 | 3.200 |
| 10 | i-Paraffins | 43 | 57 | 71 | 85 | 99 | 113 | 3.200 | 4.100 |
| 11 | Cycloparaffins | 41 | 55 | 69 | 83 | 97 | 111 | 3.200 | 4.100 |
| 12 | $C_nH_{2n-8}$ | 117 | 131 | 145 | 159 | 163 | 177 | 3.200 | 4.100 |
| 13 | $C_nH_{2n-6}$ | 91 | 105 | 119 | 133 | 147 | 161 | 3.200 | 4.100 |
| 14 | $C_nH_{2n-12}$ | 141 | 155 | 169 | 183 | 197 | 211 | 3.200 | 4.100 |
| 15 | $C_nH_{2n-10}$ | 115 | 129 | 143 | 157 | 171 | 185 | 3.200 | 4.100 |
| 16 | $C_nH_{2n-18}$ | 178 | 191 | 205 | 219 | 233 | 247 | 3.200 | 4.100 |
| . | . | . | . | . | . | . | . | . | . |
| 137 | n-C24 | 43 | 57 | 71 | 85 | 99 | 338 | 10.912 | 10.964 |
| 138 | i-Paraffins | 43 | 57 | 71 | 85 | 99 | 113 | 10.964 | 14.800 |
| 139 | Cycloparaffins | 41 | 55 | 69 | 83 | 97 | 111 | 10.964 | 14.800 |
| 140 | $C_nH_{2n-8}$ | 117 | 131 | 145 | 159 | 163 | 177 | 10.964 | 14.800 |
| 141 | $C_nH_{2n-6}$ | 91 | 105 | 119 | 133 | 147 | 161 | 10.964 | 14.800 |
| 142 | $C_nH_{2n-12}$ | 141 | 155 | 169 | 183 | 197 | 211 | 10.964 | 14.800 |
| 143 | $C_nH_{2n-10}$ | 115 | 129 | 143 | 157 | 171 | 185 | 10.964 | 14.800 |
| 144 | $C_nH_{2n-18}$ | 178 | 191 | 205 | 219 | 233 | 247 | 10.964 | 14.800 |

(a) Rule number, integer index
(b) Compound or group of compounds rule applies to
    i-para's    isoparaffins
    cyclopara's    alkylated 1 ring cycloparaffins
    $C_nH_{2n-6}$    alkylated benzenes
    $C_nH_{2n-8}$    alkylated indanes
    $C_nH_{2n-10}$    alkylated indenes
    $C_nH_{2n-12}$    alkylated naphthalenes
    $C_nH_{2n-18}$    alkylated phenanthrenes/anthracenes
(c) Masses used in Rule [up to n may be specified, where n is an integer which is equal to the number of masses scanned during the time internal (d) either in full scan mode or selected ion monitoring mode].
(d) Retention time for both starting and ending expected retention times based on historical averages in minutes.

A reference retention time is then determined for each mass spectral ion grouping selected for use in the Chemist's Rules for each of the selected compound types or specific molecules identified in Table 3. Such corrections are necessary due to slight shifts in retention times which may result from column degradation, column head pressure fluctuations, changes in column carrier gas linear velocity, or minor fluctuations in the GC column oven temperatures or other causes. The calibration step generates a series of correction factors for the entire GC/MS data file. The results of applying such corrections are shown in Table 4.

TABLE 4

| MASS (a) | RETENTION TIME (b) | TYPE (c) | LIMIT (d) | CALIBRATION TIME (e) | CORRECTION (f) |
|---|---|---|---|---|---|
| 92 | 2.812 | P | 0.200 | 2.807 | −0.005 |
| 106 | 3.840 | P | 0.200 | 3.866 | 0.026 |
| 128 | 4.800 | P | 0.200 | 4.800 | 0.000 |
| 156 | 5.554 | P | 0.200 | 5.536 | −0.018 |
| 184 | 6.667 | P | 0.200 | 6.675 | 0.008 |
| 226 | 8.058 | P | 0.200 | 8.068 | 0.010 |
| 178 | 9.000 | P | 0.300 | 9.006 | 0.006 |
| 282 | 9.555 | P | 0.200 | 9.559 | 0.004 |

(a) Mass or compound selected for the calibration
(b) Expected occurrence time, typically based on average of several analyses
(c) P = peak or maximum occurrence, F = first occurrence of the material
(d) Range (± minutes) for reference compound
(e) Observed retention time for reference material
(f) Correction to be applied between reference materials (column a). Correction for first material is from initial time to calibration time; correction for second material is between first and second reference materials; and last correction is applied to end of data acquisition.

Once the correction coefficients are determined, the actual Rules are then determined. In the case of cetane number prediction, a total of 144 Rules are used based on compound or compound series identification. For each Rule, a set of characteristic mass numbers is determined. These characteristic mass numbers can range from one to n, where n is an integer representing the entire mass range scanned or the number of selected ions monitored. In this case, six characteristic mass numbers are illustrated. The ion intensities of the masses for each Rule are summed within the upper and lower retention time limits for that Rule. The results are shown for a sampling of the 144 Rules in Table 5 for this demonstration analysis. Table 5 in its entirely is given as a table following Example 4.

TABLE 5

CHEMIST'S RULES FOR DISTILLATES WITH CORRECTIONS

Total Raw Abundance (TIC): 264722694
Chemist Rule: 120067945 (45.356%)
Air Leakage: 251310 (0.095%)
Avg Scan Rate (Min/Max): 215 (215/216)
Number of Records: 4168

| Rules a) | Compound b) | Masses c) | | | | | | | | Start d) | End e) | CStart f) | CEnd h) | Corr g) | Corr i) | Abundance j) |
|---|---|---|---|---|---|---|---|---|---|---|---|---|---|---|---|---|
| 1 | Paraffins | 43 | 57 | 71 | 85 | 99 | 113 | | | 0.400 | 3.162 | 0.399 | 3.168 | -0.001 | 0.006 | 32408 (0.027%) |
| 2 | Cyclopara's | 41 | 55 | 69 | 83 | 97 | 111 | | | 0.400 | 3.162 | 0.399 | 3.168 | -0.001 | 0.006 | 63441 (0.053%) |
| 3 | Toluene | 91 | 92 | | | | | | | 0.400 | 2.860 | 0.399 | 2.856 | -0.001 | -0.004 | 223588 (0.186%) |
| 4 | CnH2n-8 | 117 | 131 | 145 | 159 | 163 | 177 | | | 2.851 | 3.162 | 2.847 | 3.168 | -0.004 | 0.006 | 0 (0.000%) |
| 5 | CnH2n-6 | 91 | 105 | 119 | 133 | 147 | 161 | | | 2.851 | 3.162 | 2.847 | 3.168 | -0.004 | 0.006 | 0 (0.000%) |
| 6 | CnH2n-12 | 141 | 155 | 169 | 183 | 197 | 211 | | | 2.851 | 3.162 | 2.847 | 3.168 | -0.004 | 0.006 | 0 (0.000%) |
| 7 | CnH2n-10 | 115 | 129 | 143 | 157 | 171 | 185 | | | 2.851 | 3.162 | 2.847 | 3.168 | -0.004 | 0.006 | 0 (0.000%) |
| 8 | CnH2n-18 | 178 | 191 | 205 | 219 | 233 | 247 | | | 2.851 | 3.162 | 2.847 | 3.168 | -0.004 | 0.006 | 0 (0.000%) |
| 9 | n-C8 | 43 | 57 | 71 | 85 | 99 | 114 | | | 3.162 | 3.200 | 3.168 | 3.207 | 0.006 | 0.007 | 13814 (0.012%) |
| 10 | i-Paraffins | 43 | 57 | 71 | 85 | 99 | 113 | | | 3.200 | 4.100 | 3.207 | 4.119 | 0.007 | 0.019 | 121248 (0.101%) |
| 11 | Cyclopara's | 41 | 55 | 69 | 83 | 97 | 111 | | | 3.200 | 4.100 | 3.207 | 4.119 | 0.007 | 0.019 | 216183 (0.180%) |
| 12 | CnH2n-8 | 117 | 131 | 145 | 159 | 163 | 177 | | | 3.200 | 4.100 | 3.207 | 4.119 | 0.007 | 0.019 | 0 (0.000%) |
| 13 | CnH2n-6 | 91 | 105 | 119 | 133 | 147 | 161 | | | 3.200 | 4.100 | 3.207 | 4.119 | 0.007 | 0.019 | 258820 (0.216%) |
| 14 | CnH2n-12 | 141 | 155 | 169 | 183 | 197 | 211 | | | 3.200 | 4.100 | 3.207 | 4.119 | 0.007 | 0.019 | 0 (0.000%) |
| 15 | CnH2n-10 | 115 | 129 | 143 | 157 | 171 | 185 | | | 3.200 | 4.100 | 3.207 | 4.119 | 0.007 | 0.019 | 0 (0.000%) |
| 16 | CnH2n-18 | 178 | 191 | 205 | 219 | 233 | 247 | | | 3.200 | 4.100 | 3.207 | 4.119 | 0.007 | 0.019 | 0 (0.000%) |
| . | . | | | | | | | | | | | | | | | |
| 137 | n-C24 | 43 | 57 | 71 | 85 | 99 | 113 | 338 | | 10.912 | 10.964 | 10.916 | 10.968 | 0.004 | 0.004 | 21521 (0.018%) |
| 138 | i-Paraffins | 43 | 57 | 71 | 85 | 99 | 113 | | | 10.964 | 14.800 | 10.968 | 14.804 | 0.004 | 0.004 | 10799 (0.009%) |
| 139 | Cyclopara. | 41 | 55 | 69 | 83 | 97 | 111 | | | 10.964 | 14.800 | 10.968 | 14.804 | 0.004 | 0.004 | 2092 (0.002%) |
| 140 | CnH2n-8 | 117 | 131 | 145 | 159 | 163 | 177 | | | 10.964 | 14.800 | 10.968 | 14.804 | 0.004 | 0.004 | 0 (0.000%) |
| 141 | CnH2n-6 | 91 | 105 | 119 | 133 | 147 | 161 | | | 10.964 | 14.800 | 10.968 | 14.904 | 0.004 | 0.004 | 0 (0.000%) |
| 142 | CnH2n-12 | 141 | 155 | 169 | 183 | 197 | 211 | | | 10.964 | 14.800 | 10.968 | 14.904 | 0.004 | 0.004 | 0 (0.000%) |
| 143 | CnH2n-10 | 115 | 129 | 143 | 157 | 171 | 185 | | | 10.964 | 14.800 | 10.968 | 14.804 | 0.004 | 0.004 | 0 (0.000%) |
| 144 | CnH2n-18 | 178 | 191 | 205 | 219 | 233 | 247 | | | 10.964 | 14.800 | 10.968 | 14.804 | 0.004 | 0.004 | 0 (0.000%) |

Sum = 120067945 (100.000%)

a) Rule number, integer index
b) Compound or group of compounds rule applies to:
   cyclopara's    alkylated 1 ring cycloparaffins
   $C_nH_{2n-6}$  alkylated benzenes
   $C_nH_{2n-8}$  alkylated indanes
   $C_nH_{2n-10}$ alkylated indenes
   $C_nH_{2n-12}$ alkylated naphthalenes
   $C_nH_{2n-18}$ alkylated phenanthrenes/anthracenes
c) Masses used in Rule [up to n may be specified, where n is an integer which is equal to the number of masses scanned during the time interval (d to e) either in full scan mode or selected ion monitoring mode].
d) start retention time in minutes TABLE 5-continued

CHEMIST'S RULES FOR DISTILLATES WITH CORRECTIONS

| | | | | | | | | | |
|---|---|---|---|---|---|---|---|---|---|
| Total Raw Abundance (TIC): | 264722694 | | | | | | | | |
| Chemist Rule: | 120067945 | (45.356%) | | | | | | | |
| Air Leakage: | 251310 | (0.095%) | | | | | | | |
| Avg Scan Rate (Min/Max): | 215 | (215/216) | | | | | | | |
| Number of Records: | 4168 | | | | | | | | |
| Rules a) Compound b) | | Masses c) | Start d) | End e) | CStart f) | Corr g) | CEnd h) | Corr i) | Abundance j) | e) end retention time in minutes
f) corrected start retention time
g) correction = difference between start and cstart (in minutes)
h) corrected end retention time
i) correction = difference between end and cend (in minutes)
j) Abundance, both as total sum and as normalized percentage based on Chemist's Rules Total Raw Abundance (TIC): Total area observed in the GC/MS analysis.

Chemist Rule: Total area found using the Chemist's Rules; based on experience, should be greater than 30% of total raw abundance.

Air Leakage: Total ionization due to air (m/z 28, 32, 40, 44) useful diagnostic for instrumental problems.

Average scan rate (Min/Max): Shows the minimum, average and maximum scan rates during the GC/MS analysis and is a useful diagnostic to identify instrumental problems.

Number of records: Is the number of mass spectral scans acquired during the analysis.

The analysis summarized in Table 5 is done for each reference sample. The results from these respective analyses form a training set which is subjected to mathematical treatment. The goal is to develop a model that can be used to predict the unknown properties of future samples using their mass spectral data only. The mathematical treatments are described by multivariate correlation techniques such as Projection to Latent Structures (PLS) or otherwise known as Partial Least Squares (PLS), Principal Component Regression (PCR), and Ridge Regression (RR). These techniques are superior to ordinary multiple linear regression in their ability to treat collinearity amongst variables in the X-block or GC/MS data matrix (and Y-block or properties matrix for PLS), and in their ability to handle the quantity of data generated by the Chemist's Rules. Ordinary Multiple Linear Regression cannot be used to treat collinear variables.

PLS/PCR/RR are numerical analysis techniques for detecting and formulating a mathematical structure (model) within a data set comprising observations associated with multiple objects. Each object has associated with it observations for multiple variables, the latter being common to all objects. These multiple variables are assigned into two categories, known as X-block and Y-block. Observations associated with all variables in the X-block are realized from a common process (GC/MS data in this case). Observations associated with variables in the Y-block (known properties in this case) are realized from processes that may be different for each variable. The data set used to construct this mathematical model is referred to as the model calibration data set.

The common use of PLS/PCR/RR is to apply the model developed from the calibration data set to X-block observations realized for new objects (not in the calibration data set) to predict values for the corresponding variables in the Y-block for these new objects, without having to execute the Y-block processes used in the calibration data set. Using diagnostics that are simultaneously generated by the PLS/PCR/RR model, assessment of whether the new objects can be adequately described by the model, and whether the model is used in an extrapolation mode versus interpolation mode can be performed.

PLS/PCR addresses the collinearity features in the X-block and Y-block, by suitably reducing the dimensionally in both X- and Y-blocks (for PLS), and X-block only (for PCR) to form the model. Collinearity is a term referring to the existence of relationships between variables within the block itself. In the PLS modeling algorithm a number of independent dimensions in the X- and Y-blocks are identified by forming pseudo-variables known as principal components or latent vectors through different sets of linear combinations of original variables in each block. Each set of such combinations constitutes an independent dimension. It comprises a set of coefficients that each value associated with each variable in the block is to be weighted by to arrive at the new value for this dimension. The values for the new, reduced dimensions in the Y-block are regressed onto their counterparts in the new, reduced dimensions of the X-block to arrive at the most parsimonious dimension size (number of latent vectors) and their associated weights, with the final goal of one linear equation generated to permit prediction of Y-block variables using X-block variables. The number of dimensions used to construct the model is determined through optimization of a criterion known as PRESS (Prediction Error Sum of Squares), cumulated by a Cross Validation (CV) technique using the training data set, and, following the general model parsimony principle.

For PCR, the number of independent dimensions in the X-block are first selected and identified in a similar fashion as in PLS by forming principal components. Then, for each variable in the Y-block, a model is obtained by performing ordinary multiple linear regression using the Principal Components as "Prediction Variables".

For Ridge Regression, the collinearity problem is dealt with in a different manner than PLS/PCR. Here a diagonal matrix known as the Lambda Matrix is added to the Covariance Matrix of the X-block with the net effect of stabilizing the numerical computation needed to obtain the model coefficients. The selection of Lambda values is through optimization of PRESS criterion using cross validation of the training set.

Thus, the Chemist's Rule data for the various reference samples and derived from GC/MS analysis form the X-block variables. PLS/PCR/RR treatment may require preliminary reorganization of the X-block data, such as transposition and removal of redundant data and constants or mathematical transformations. The Y-block variables are the property (or properties) to be predicted, and may also require mathematical transformations such as logarithmic or geometric, as well as reorganization. The data blocks may be represented by:

X-BlockMatrix

[Chemist's Rules (n samples × 144 columns)]

$$\begin{vmatrix} X_{1,1} & X_{1,2} & X_{1,3} & \ldots & X_{1,142} & X_{1,143} & X_{1,144} \\ X_{2,1} & X_{2,2} & X_{2,3} & \ldots & X_{2,142} & X_{2,143} & X_{2,144} \\ X_{3,1} & X_{3,2} & X_{3,3} & \ldots & X_{3,142} & X_{3,143} & X_{3,144} \\ . & . & . & & . & . & . \\ . & . & . & & . & . & . \\ . & . & . & & . & . & . \\ X_{n,1} & X_{n,2} & X_{n,3} & \ldots & X_{n,142} & X_{n,143} & X_{n,144} \end{vmatrix}$$

[Measured Property (n samples)]

$$\begin{vmatrix} y_1 \\ y_2 \\ y_3 \\ . \\ . \\ . \\ y_n \end{vmatrix}$$

The Y-block may be a single observation per set of Chemist's Rules as shown above, or it may be a n x m matrix of observations, where there are m different properties to be predicted.

The results of PLS/PCR/RR treatment of the training set data are a series of coefficients. Raw GC/MS data from an unknown sample (or samples) are then treated by the Chemist's Rules first to correct the retention times and then to form the ion summations. Each value for the Chemist's Rule ion summation is then multiplied by the training set coefficients and summed to generate the prediction of the desired property or properties. Table 6 illustrates the quality of the predicted cetane values for both the training set and the unknown test set.

TABLE 6

| PREDICTED VS. MEASURED CETANE VALUES | | |
| --- | --- | --- |
| SAMPLE | MEASURED* | PREDICTED |
| Training Set | | |
| A | 32.6 | 32.3 |
| C | 34.1 | 34.3 |
| D | 35.0 | 35.2 |
| F | 37.4 | 37.2 |
| G | 38.5 | 38.2 |

TABLE 6-continued

PREDICTED VS. MEASURED CETANE VALUES

| SAMPLE | MEASURED* | PREDICTED |
|---|---|---|
| I | 40.0 | 40.1 |
| J | 41.0 | 41.2 |
| L | 43.2 | 43.3 |
| HCISDIST | 43.8 | 43.7 |
| CLHO | 15.0 | 15.0 |
| HAGO | 44.9 | 44.9 |
| LOPOUR | 44.1 | 44.1 |
| SRLGO | 54.7 | 54.7 |
| Test Set | | |
| B | 33.5 | 33.4 |
| E | 36.3 | 36.3 |
| H | 39.2 | 39.1 |
| K | 42.0 | 42.2 |
| M | 43.9 | 44.3 |
| N | 45.3 | 45.2 |

*measured by ASTM D 613-86

EXAMPLE 2

The procedure of Example 1 was repeated for predicting aniline point for diesel fuel blends. Samples A, C, D, F, G, I, J, L, and N were used to form the training set and samples B, E, H, K, and M formed the test set. The results for the aniline point prediction are summarized in Table 7.

TABLE 7

PREDICTED VS. MEASURED ANILINE POINT (°C.)

| MEASURED* | PREDICTED |
|---|---|
| Training Set | |
| 36.8 | 37.1 |
| 41.6 | 41.5 |
| 43.3 | 43.3 |
| 47.1 | 47.0 |
| 49.2 | 48.9 |
| 52.9 | 52.8 |
| 54.6 | 54.5 |
| 58.7 | 58.6 |
| 61.8 | 62.2 |
| Test Set | |
| 39.2 | 39.6 |
| 45.8 | 45.1 |
| 51.6 | 50.8 |
| 56.7 | 56.6 |
| 60.3 | 60.4 |

*measured by ASTM D 611-82 (1987)

EXAMPLE 3

The procedure of Example 1 was repeated for predicting density for diesel fuel blends. Samples A, C, D, F, G, I, J, L, and N were used to form the training set and samples B, E, H, K, and M formed the test set. The results for density prediction are summarized in Table 8.

TABLE 8

PREDICTED VS. MEASURED DENSITY AT 15° C. (g/ml)

| MEASURED* | PREDICTED |
|---|---|
| Training Set | |
| 0.8820 | 0.8829 |
| 0.8797 | 0.8793 |
| 0.8760 | 0.8760 |
| 0.8684 | 0.8682 |
| 0.8644 | 0.8641 |
| 0.8567 | 0.8566 |
| 0.8531 | 0.8530 |
| 0.8452 | 0.8445 |
| 0.8405 | 0.8416 |
| Test Set | |
| 0.8836 | 0.8824 |
| 0.8720 | 0.8718 |
| 0.8606 | 0.8605 |
| 0.8490 | 0.8486 |
| 0.8417 | 0.8408 |

*measured by ASTM D 5002-89

EXAMPLE 4

The procedure of Example 1 was repeated for predicting distillation T50 values, the temperature at which 50% of the sample has distilled. The training and test sets were as described in Examples 2 and 3. Results are shown in Table 9.

TABLE 9

PREDICTED VS. MEASURED DISTILLATION T50 (°C.)

| MEASURED* | PREDICTED |
|---|---|
| Training Set | |
| 262 | 262 |
| 261 | 261 |
| 259 | 259 |
| 258 | 258 |
| 256 | 256 |
| 257 | 257 |
| 255 | 255 |
| 252 | 252 |
| 254 | 254 |
| Test Set | |
| 261 | 262 |
| 258 | 259 |
| 255 | 257 |
| 252 | 254 |
| 251 | 252 |

*measured by ASTM D 86-90

Other properties of diesel fuel blends such as cloud point, flash point, viscosity, pour point, heat content, distillation characteristics, LTFT, FFFT, etc., could be predicted using the method according to the invention. The subject method can also be used to predict properties of other types of complex hydrocarbon mixtures boiling below 350° C.

| COMPLETE CHEMIST'S RULES FOR DISTILLATES |||||||||
|---|---|---|---|---|---|---|---|---|
| | | | | | | | Retention Time (d) ||
| Rule (a) | Compound (b) | Mass (c) | | | | | Start | End |
| 1 | Paraffins | 43 | 57 | 71 | 85 | 99 | 113 | 0.400 | 3.162 |
| 2 | Cyclopara's | 41 | 55 | 69 | 83 | 97 | 111 | 0.400 | 3.162 |
| 3 | Toluene | 91 | 92 | | | | | 0.400 | 2.860 |
| 4 | CnH2n-8 | 117 | 131 | 145 | 159 | 163 | 177 | 2.851 | 3.162 |
| 5 | CnH2n-6 | 91 | 105 | 119 | 133 | 147 | 161 | 2.851 | 3.162 |
| 6 | CnH2n-12 | 141 | 155 | 169 | 183 | 197 | 211 | 2.851 | 3.162 |
| 7 | CnH2n-10 | 115 | 129 | 143 | 157 | 171 | 185 | 2.851 | 3.162 |
| 8 | CnH2n-18 | 178 | 191 | 205 | 219 | 233 | 247 | 2.851 | 3.162 |
| 9 | n-C8 | 43 | 57 | 71 | 85 | 99 | 114 | 3.162 | 3.200 |
| 10 | i-Para's | 43 | 57 | 71 | 85 | 99 | 113 | 3.200 | 4.100 |
| 11 | Cyclopara's | 41 | 55 | 69 | 83 | 97 | 111 | 3.200 | 4.100 |
| 12 | CnH2n-8 | 117 | 131 | 145 | 159 | 163 | 177 | 3.200 | 4.100 |
| 13 | CnH2n-6 | 91 | 105 | 119 | 133 | 147 | 161 | 3.200 | 4.100 |
| 14 | CnH2n-12 | 141 | 155 | 169 | 183 | 197 | 211 | 3.200 | 4.100 |
| 15 | CnH2n-10 | 115 | 129 | 143 | 157 | 171 | 185 | 3.200 | 4.100 |
| 16 | CnH2n-18 | 178 | 191 | 205 | 219 | 233 | 247 | 3.200 | 4.100 |
| 17 | n-C9 | 43 | 57 | 71 | 85 | 99 | 128 | 4.100 | 41.50 |
| 18 | i-Para's | 43 | 57 | 71 | 85 | 99 | 113 | 4.150 | 4.880 |
| 19 | Cyclopara's | 41 | 55 | 69 | 83 | 97 | 111 | 4.150 | 4.880 |
| 20 | CnH2n-8 | 117 | 131 | 145 | 159 | 163 | 177 | 4.150 | 4.880 |
| 21 | CnH2n-6 | 91 | 105 | 119 | 133 | 147 | 161 | 4.150 | 4.880 |
| 22 | CnH2n-12 | 128 | 141 | 155 | 169 | 183 | 197 | 4.150 | 4.880 |
| 23 | CnH2n-10 | 115 | 129 | 143 | 157 | 171 | 185 | 4.150 | 4.880 |
| 24 | CnH2n-18 | 178 | 191 | 205 | 219 | 233 | 247 | 4.150 | 4.880 |
| 25 | n-C10 | 43 | 57 | 71 | 85 | 99 | 142 | 4.880 | 4.901 |
| 26 | i-Para's | 43 | 57 | 71 | 85 | 99 | 113 | 4.900 | 5.520 |
| 27 | Cyclopara's | 41 | 55 | 69 | 83 | 97 | 111 | 4.900 | 5.520 |
| 28 | CnH2n-8 | 117 | 131 | 145 | 159 | 163 | 177 | 4.900 | 5.520 |
| 29 | CnH2n-6 | 91 | 105 | 119 | 133 | 147 | 161 | 4.900 | 5.520 |
| 30 | CnH2n-12 | 141 | 155 | 169 | 183 | 197 | 211 | 4.900 | 5.520 |
| 31 | CnH2n-10 | 115 | 129 | 143 | 157 | 171 | 185 | 4.900 | 5.520 |
| 32 | CnH2n-18 | 178 | 191 | 205 | 219 | 233 | 247 | 4.900 | 5.520 |
| 33 | n-C11 | 43 | 57 | 71 | 85 | 99 | 156 | 5.200 | 5.580 |
| 34 | i-Para's | 43 | 57 | 71 | 85 | 99 | 113 | 5.580 | 6.153 |
| 35 | Cyclopara's | 41 | 55 | 69 | 83 | 97 | 111 | 5.580 | 6.153 |
| 36 | CnH2n-8 | 117 | 131 | 145 | 159 | 163 | 177 | 5.580 | 6.153 |
| 37 | CnH2n-6 | 91 | 105 | 119 | 133 | 147 | 161 | 5.580 | 6.153 |
| 38 | CnH2n-12 | 141 | 155 | 169 | 183 | 197 | 211 | 5.580 | 6.153 |
| 39 | CnH2n-10 | 115 | 129 | 143 | 157 | 171 | 185 | 5.580 | 6.153 |
| 40 | CnH2n-18 | 178 | 191 | 205 | 219 | 233 | 247 | 5.580 | 6.153 |
| 41 | n-C12 | 43 | 57 | 71 | 85 | 99 | 170 | 6.153 | 6.178 |
| 42 | i-Para's | 43 | 57 | 71 | 85 | 99 | 113 | 6.178 | 6.635 |
| 43 | Cyclopara's | 41 | 55 | 69 | 83 | 97 | 111 | 6.178 | 6.635 |
| 44 | CnH2n-8 | 117 | 131 | 145 | 159 | 163 | 177 | 6.178 | 6.635 |
| 45 | CnH2n-6 | 91 | 105 | 119 | 133 | 147 | 161 | 6.178 | 6.635 |
| 46 | CnH2n-12 | 141 | 155 | 169 | 183 | 197 | 211 | 6.178 | 6.635 |
| 47 | CnH2n-10 | 115 | 129 | 143 | 157 | 171 | 185 | 6.178 | 6.635 |
| 48 | CnH2n-18 | 178 | 191 | 205 | 219 | 233 | 247 | 6.178 | 6.635 |
| 49 | n-C13 | 43 | 57 | 71 | 85 | 99 | 184 | 6.635 | 6.692 |
| 50 | i-Para's | 43 | 57 | 71 | 85 | 99 | 113 | 6.692 | 7.124 |
| 51 | Cyclopara's | 41 | 55 | 69 | 83 | 97 | 111 | 6.692 | 7.124 |
| 52 | CnH2n-8 | 117 | 131 | 145 | 159 | 163 | 177 | 6.692 | 7.124 |
| 53 | CnH2n-6 | 91 | 105 | 119 | 133 | 147 | 161 | 6.692 | 7.124 |
| 54 | CnH2n-12 | 141 | 155 | 169 | 183 | 197 | 211 | 6.692 | 7.124 |
| 55 | CnH2n-10 | 115 | 129 | 143 | 157 | 171 | 185 | 6.692 | 7.124 |
| 56 | CnH2n-18 | 178 | 191 | 205 | 219 | 233 | 247 | 6.692 | 7.124 |
| 57 | n-C14 | 43 | 57 | 71 | 85 | 99 | 198 | 7.124 | 7.184 |
| 58 | i-Para's | 43 | 57 | 71 | 85 | 99 | 113 | 7.124 | 7.593 |
| 59 | Cyclopara's | 41 | 55 | 69 | 83 | 97 | 111 | 7.124 | 7.593 |
| 60 | CnH2n-8 | 117 | 131 | 145 | 159 | 163 | 177 | 7.124 | 7.593 |
| 61 | CnH2n-6 | 91 | 105 | 119 | 133 | 147 | 161 | 7.124 | 7.593 |
| 62 | CnH2n-12 | 141 | 155 | 169 | 183 | 197 | 211 | 7.124 | 7.593 |
| 63 | CnH2n-10 | 115 | 129 | 143 | 157 | 171 | 185 | 7.124 | 7.593 |
| 64 | CnH2n-18 | 178 | 191 | 205 | 219 | 233 | 247 | 7.124 | 7.593 |
| 65 | n-C15 | 43 | 57 | 71 | 85 | 99 | 212 | 7.593 | 7.645 |
| 66 | i-Para's | 43 | 57 | 71 | 85 | 99 | 113 | 7.645 | 8.016 |
| 67 | Cyclopara's | 41 | 55 | 69 | 83 | 97 | 111 | 7.645 | 8.016 |
| 68 | CnH2n-8 | 117 | 131 | 145 | 159 | 163 | 177 | 7.645 | 8.016 |
| 69 | CnH2n-6 | 91 | 105 | 119 | 133 | 147 | 161 | 7.645 | 8.016 |
| 70 | CnH2n-12 | 141 | 155 | 169 | 183 | 197 | 211 | 7.645 | 8.016 |
| 71 | CnH2n-10 | 115 | 129 | 143 | 157 | 171 | 185 | 7.645 | 8.016 |
| 72 | CnH2n-18 | 178 | 191 | 205 | 219 | 233 | 247 | 7.645 | 8.016 |
| 73 | n-C16 | 43 | 57 | 71 | 85 | 99 | 226 | 8.016 | 8.079 |
| 74 | i-Para's | 43 | 57 | 71 | 85 | 99 | 113 | 8.079 | 8.430 |

-continued

COMPLETE CHEMIST'S RULES FOR DISTILLATES

| Rule (a) | Compound (b) | Mass (c) | | | | | | Retention Time (d) | |
|---|---|---|---|---|---|---|---|---|---|
| | | | | | | | | Start | End |
| 75 | Cyclopara's | 41 | 55 | 69 | 83 | 97 | 111 | 8.079 | 8.430 |
| 76 | CnH2n-8 | 117 | 131 | 145 | 159 | 163 | 177 | 8.079 | 8.430 |
| 77 | CnH2n-6 | 91 | 105 | 119 | 133 | 147 | 161 | 8.079 | 8.430 |
| 78 | CnH2n-12 | 141 | 155 | 169 | 183 | 197 | 211 | 8.079 | 8.430 |
| 79 | CnH2n-10 | 115 | 129 | 143 | 157 | 171 | 185 | 8.079 | 8.430 |
| 80 | CnH2n-18 | 178 | 191 | 205 | 219 | 233 | 247 | 8.079 | 8.430 |
| 81 | n-C17 | 43 | 57 | 71 | 85 | 99 | 240 | 8.430 | 8.476 |
| 82 | i-Para's | 43 | 57 | 71 | 85 | 99 | 113 | 8.476 | 8.808 |
| 83 | Cyclopara's | 41 | 55 | 69 | 83 | 97 | 111 | 8.476 | 8.808 |
| 84 | CnH2n-8 | 117 | 131 | 145 | 159 | 163 | 177 | 8.476 | 8.808 |
| 85 | CnH2n-6 | 91 | 105 | 119 | 133 | 147 | 161 | 8.476 | 8.808 |
| 86 | CnH2n-12 | 141 | 155 | 169 | 183 | 197 | 211 | 8.476 | 8.808 |
| 87 | CnH2n-10 | 115 | 129 | 143 | 157 | 171 | 185 | 8.476 | 8.808 |
| 88 | CnH2n-18 | 178 | 191 | 205 | 219 | 233 | 247 | 8.476 | 8.808 |
| 89 | n-C18 | 43 | 57 | 71 | 85 | 99 | 254 | 8.808 | 8.866 |
| 90 | i-Para's | 43 | 57 | 71 | 85 | 99 | 113 | 8.866 | 9.187 |
| 91 | Cyclopara's | 41 | 55 | 69 | 83 | 97 | 111 | 8.866 | 9.187 |
| 92 | CnH2n-8 | 117 | 131 | 145 | 159 | 163 | 177 | 8.866 | 9.187 |
| 93 | CnH2n-6 | 91 | 105 | 119 | 133 | 147 | 161 | 8.866 | 9.187 |
| 94 | CnH2n-12 | 141 | 155 | 169 | 183 | 197 | 211 | 8.866 | 9.187 |
| 95 | CnH2n-10 | 115 | 129 | 143 | 157 | 171 | 185 | 8.866 | 9.187 |
| 96 | CnH2n-18 | 178 | 191 | 205 | 219 | 233 | 247 | 8.866 | 9.187 |
| 97 | n-C19 | 43 | 57 | 71 | 85 | 99 | 268 | 9.187 | 9.234 |
| 98 | i-Para's | 43 | 57 | 71 | 85 | 99 | 113 | 9.234 | 9.523 |
| 99 | Cyclopara's | 41 | 55 | 69 | 83 | 97 | 111 | 9.234 | 9.523 |
| 100 | CnH2n-8 | 117 | 131 | 145 | 159 | 163 | 177 | 9.234 | 9.523 |
| 101 | CnH2n-6 | 91 | 105 | 119 | 133 | 147 | 161 | 9.234 | 9.523 |
| 102 | CnH2n-12 | 141 | 155 | 169 | 183 | 197 | 211 | 9.234 | 9.523 |
| 103 | CnH2n-10 | 115 | 129 | 143 | 157 | 171 | 185 | 9.234 | 9.523 |
| 104 | CnH2n-18 | 178 | 191 | 205 | 219 | 233 | 247 | 9.234 | 9.523 |
| 105 | n-C20 | 43 | 57 | 71 | 85 | 99 | 282 | 9.523 | 9.578 |
| 106 | i-Para's | 43 | 57 | 71 | 85 | 99 | 113 | 9.578 | 9.860 |
| 107 | Cyclopara's | 41 | 55 | 69 | 83 | 97 | 111 | 9.578 | 9.860 |
| 108 | CnH2n-8 | 117 | 131 | 145 | 159 | 163 | 177 | 9.578 | 9.860 |
| 109 | CnH2n-6 | 91 | 105 | 119 | 133 | 147 | 161 | 9.578 | 9.860 |
| 110 | CnH2n-12 | 141 | 155 | 169 | 183 | 197 | 211 | 9.578 | 9.860 |
| 111 | CnH2n-10 | 115 | 129 | 143 | 157 | 171 | 185 | 9.578 | 9.860 |
| 112 | CnH2n-18 | 178 | 191 | 205 | 219 | 233 | 247 | 9.578 | 9.860 |
| 113 | n-C21 | 43 | 57 | 71 | 85 | 99 | 296 | 9.860 | 9.912 |
| 114 | i-Para's | 43 | 57 | 71 | 85 | 99 | 113 | 9.912 | 10.163 |
| 115 | Cyclopara's | 41 | 55 | 69 | 83 | 97 | 111 | 9.912 | 10.163 |
| 116 | CnH2n-8 | 117 | 131 | 145 | 159 | 163 | 177 | 9.912 | 10.163 |
| 117 | CnH2n-6 | 91 | 105 | 119 | 133 | 147 | 161 | 9.912 | 10.163 |
| 118 | CnH2n-12 | 141 | 155 | 169 | 183 | 197 | 211 | 9.912 | 10.163 |
| 119 | CnH2n-10 | 115 | 129 | 143 | 157 | 171 | 185 | 9.912 | 10.163 |
| 120 | CnH2n-18 | 178 | 191 | 205 | 219 | 233 | 247 | 9.912 | 10.163 |
| 121 | n-C22 | 43 | 57 | 71 | 85 | 99 | 310 | 10.163 | 10.266 |
| 122 | i-Para's | 43 | 57 | 71 | 85 | 99 | 113 | 10.266 | 10.519 |
| 123 | Cyclopara's | 41 | 55 | 69 | 83 | 97 | 111 | 10.266 | 10.519 |
| 124 | CnH2n-8 | 117 | 131 | 145 | 159 | 163 | 177 | 10.266 | 10.519 |
| 125 | CnH2n-6 | 91 | 105 | 119 | 133 | 147 | 161 | 10.266 | 10.519 |
| 126 | CnH2n-12 | 141 | 155 | 169 | 183 | 197 | 211 | 10.266 | 10.519 |
| 127 | CnH2n-10 | 115 | 129 | 143 | 157 | 171 | 185 | 10.266 | 10.519 |
| 128 | CnH2n-18 | 178 | 191 | 205 | 219 | 233 | 247 | 10.266 | 10.519 |
| 129 | n-C23 | 43 | 57 | 71 | 85 | 99 | 324 | 10.519 | 10.619 |
| 130 | i-Para's | 43 | 57 | 71 | 85 | 99 | 113 | 10.619 | 10.912 |
| 131 | Cyclopara's | 41 | 55 | 69 | 83 | 97 | 111 | 10.619 | 10.912 |
| 132 | CnH2n-8 | 117 | 131 | 145 | 159 | 163 | 177 | 10.619 | 10.912 |
| 133 | CnH2n-6 | 91 | 105 | 119 | 133 | 147 | 161 | 10.619 | 10.912 |
| 134 | CnH2n-12 | 141 | 155 | 169 | 183 | 197 | 211 | 10.619 | 10.912 |
| 135 | CnH2n-10 | 115 | 129 | 143 | 157 | 171 | 185 | 10.619 | 10.912 |
| 136 | CnH2n-18 | 178 | 191 | 205 | 219 | 233 | 247 | 10.619 | 10.912 |
| 137 | n-C24 | 43 | 57 | 71 | 85 | 99 | 338 | 10.912 | 10.964 |
| 138 | i-Para's | 43 | 57 | 71 | 85 | 99 | 113 | 10.964 | 14.800 |
| 139 | Cyclopara's | 41 | 55 | 69 | 83 | 97 | 111 | 10.964 | 14.800 |
| 140 | CnH2n-8 | 117 | 131 | 145 | 159 | 163 | 177 | 10.964 | 14.800 |
| 141 | CnH2n-6 | 91 | 105 | 119 | 133 | 147 | 161 | 10.964 | 14.800 |
| 142 | CnH2n-12 | 141 | 155 | 169 | 183 | 197 | 211 | 10.964 | 14.800 |
| 143 | CnH2n-10 | 115 | 129 | 143 | 157 | 171 | 185 | 10.964 | 14.800 |
| 144 | CnH2n-18 | 178 | 191 | 205 | 219 | 233 | 247 | 20.964 | 14.800 |

(a) Rule number, integer index
(b) Compound or group of compounds rule applies to
    i-para's       isoparaffins

COMPLETE CHEMIST'S RULES FOR DISTILLATES

| | | | Retention Time (d) | |
|---|---|---|---|---|
| Rule (a) | Compound (b) | Mass (c) | Start | End |
| | cyclopara's | alkylated 1 ring cycloparaffins | | |
| | $C_nH_{2n-6}$ | alkylated benzenes | | |
| | $C_nH_{2n-8}$ | alkylated indanes | | |
| | $C_nH_{2n-10}$ | alkylated indenes | | |
| | $C_nH_{2n-12}$ | alkylated naphthalenes | | |
| | $C_nH_{2n-18}$ | alkylated phenanthrenes/anthracenes | | |

(c) Masses used in Rule [up to n may be specified, where n is an integer which is equal to the number of masses scanned during the time interval (d) either in full scan mode or selected ion monitoring mode].

(d) Retention time for both starting and ending expected retention times based on historical averages in minutes.

COMPLETE CHEMIST'S RULES FOR DISTILLATES WITH CORRECTIONS

Total Raw Abundance (TIC): 264722694  
Chemist Rule: 120067945 (45.356%)  
Air Leakage: 251310 (0.095%)  
Avg Scan Rate (Min/Max): 215 (215/216)  
Number of Records: 4168

| Rule[a] | Compound[b] | Masses[c] | | | | | | | | Start[d] | End[e] | CStart[f] | Corr[g] | CEnd[h] | Corr[i] | Abundance[j] | |
|---|---|---|---|---|---|---|---|---|---|---|---|---|---|---|---|---|---|
| 1 | Paraffins | 43 | 57 | 71 | 85 | 99 | 113 | | | 0.400 | 3.162 | 0.399 | −0.001 | 3.168 | 0.006 | 32408 | (0.027%) |
| 2 | Cyclopara. | 41 | 55 | 69 | 83 | 97 | 111 | | | 0.400 | 3.162 | 0.399 | −0.001 | 3.168 | 0.006 | 63441 | (0.053%) |
| 3 | Toluene | 91 | 92 | | | | | | | 0.400 | 2.860 | 0.399 | −0.001 | 2.856 | −0.004 | 223588 | (0.186%) |
| 4 | CnH2n-8 | 117 | 131 | 145 | 159 | 163 | 177 | | | 2.851 | 3.162 | 2.847 | −0.004 | 3.168 | 0.006 | 0 | (0.000%) |
| 5 | CnH2n-6 | 91 | 105 | 119 | 133 | 147 | 161 | | | 2.851 | 3.162 | 2.847 | −0.004 | 3.168 | 0.006 | 0 | (0.000%) |
| 6 | CnH2n-12 | 141 | 155 | 169 | 183 | 197 | 211 | | | 2.851 | 3.162 | 2.847 | −0.004 | 3.168 | 0.006 | 0 | (0.000%) |
| 7 | CnH2n-10 | 115 | 129 | 143 | 157 | 171 | 185 | | | 2.851 | 3.162 | 2.847 | −0.004 | 3.168 | 0.006 | 0 | (0.000%) |
| 8 | CnH2n-18 | 178 | 191 | 205 | 219 | 233 | 247 | | | 2.851 | 3.162 | 2.847 | −0.004 | 3.168 | 0.006 | 0 | (0.000%) |
| 9 | n-C8 | 43 | 57 | 71 | 85 | 99 | 114 | | | 3.162 | 3.200 | 3.168 | 0.006 | 3.207 | 0.007 | 13814 | (0.012%) |
| 10 | i-Paraffins | 43 | 57 | 71 | 85 | 99 | 113 | | | 3.200 | 4.100 | 3.207 | 0.007 | 4.119 | 0.019 | 121248 | (0.101%) |
| 11 | Cyclopara. | 41 | 55 | 69 | 83 | 97 | 111 | | | 3.200 | 4.100 | 3.207 | 0.007 | 4.119 | 0.019 | 216183 | (0.180%) |
| 12 | CnH2n-8 | 117 | 131 | 145 | 159 | 163 | 177 | | | 3.200 | 4.100 | 3.207 | 0.007 | 4.119 | 0.019 | 0 | (0.000%) |
| 13 | CnH2n-6 | 91 | 105 | 119 | 133 | 147 | 161 | | | 3.200 | 4.100 | 3.207 | 0.007 | 4.119 | 0.019 | 258820 | (0.216%) |
| 14 | CnH2n-12 | 141 | 155 | 169 | 183 | 197 | 211 | | | 3.200 | 4.100 | 3.207 | 0.007 | 4.119 | 0.019 | 0 | (0.000%) |
| 15 | CnH2n-10 | 115 | 129 | 143 | 157 | 171 | 185 | | | 3.200 | 4.100 | 3.207 | 0.007 | 4.119 | 0.019 | 0 | (0.000%) |
| 16 | CnH2n-18 | 178 | 191 | 205 | 219 | 233 | 247 | | | 3.200 | 4.100 | 3.207 | 0.007 | 4.119 | 0.019 | 0 | (0.000%) |
| 17 | n-C9 | 43 | 57 | 71 | 85 | 99 | 128 | | | 4.100 | 4.150 | 4.119 | 0.019 | 4.168 | 0.018 | 15498 | (0.013%) |
| 18 | i-Paraffins | 43 | 57 | 71 | 85 | 99 | 113 | | | 4.150 | 4.880 | 4.168 | 0.018 | 4.878 | −0.002 | 660755 | (0.550%) |
| 19 | Cyclopara. | 41 | 55 | 69 | 83 | 97 | 111 | | | 4.150 | 4.880 | 4.168 | 0.018 | 4.878 | −0.002 | 1333269 | (1.110%) |
| 20 | CnH2n-8 | 117 | 131 | 145 | 159 | 163 | 177 | | | 4.150 | 4.880 | 4.168 | 0.018 | 4.878 | −0.002 | 22151 | (0.018%) |
| 21 | CnH2n-6 | 91 | 105 | 119 | 133 | 147 | 161 | | | 4.150 | 4.880 | 4.168 | 0.018 | 4.878 | −0.002 | 1218922 | (1.015%) |
| 22 | CnH2n-12 | 141 | 155 | 169 | 183 | 197 | 211 | | | 4.150 | 4.880 | 4.168 | 0.018 | 4.878 | −0.002 | 0 | (0.000%) |
| 23 | CnH2n-10 | 115 | 129 | 143 | 157 | 171 | 185 | | | 4.150 | 4.880 | 4.168 | 0.018 | 4.878 | −0.002 | 28008 | (0.023%) |
| 24 | CnH2n-18 | 178 | 191 | 205 | 219 | 233 | 247 | | | 4.150 | 4.880 | 4.168 | 0.018 | 4.878 | −0.002 | 0 | (0.000%) |
| 25 | n-C10 | 43 | 57 | 71 | 85 | 99 | 142 | | | 4.880 | 4.901 | 4.878 | −0.002 | 4.899 | −0.002 | 289888 | (0.241%) |
| 26 | i-Paraffins | 43 | 57 | 71 | 85 | 99 | 113 | | | 4.900 | 5.520 | 4.898 | −0.002 | 5.503 | −0.017 | 1533824 | (1.277%) |
| 27 | Cyclopara. | 41 | 55 | 69 | 83 | 97 | 111 | | | 4.900 | 5.520 | 4.898 | −0.002 | 5.503 | −0.017 | 2925819 | (2.437%) |
| 28 | CnH2n-8 | 117 | 131 | 145 | 159 | 163 | 177 | | | 4.900 | 5.520 | 4.898 | −0.002 | 5.503 | −0.017 | 338162 | (0.282%) |
| 29 | CnH2n-6 | 91 | 105 | 119 | 133 | 147 | 161 | | | 4.900 | 5.520 | 4.898 | −0.002 | 5.503 | −0.017 | 2910452 | (2.424%) |
| 30 | CnH2n-12 | 141 | 155 | 169 | 183 | 197 | 211 | | | 4.900 | 5.520 | 4.898 | −0.002 | 5.503 | −0.017 | 2805 | (0.002%) |
| 31 | CnH2n-10 | 115 | 129 | 143 | 157 | 171 | 185 | | | 4.900 | 5.520 | 4.898 | −0.002 | 5.503 | −0.017 | 188499 | (0.157%) |
| 32 | CnH2n-18 | 178 | 191 | 205 | 219 | 233 | 247 | | | 4.900 | 5.520 | 4.898 | −0.002 | 5.503 | −0.017 | 0 | (0.000%) |
| 33 | n-C11 | 43 | 57 | 71 | 85 | 99 | 156 | | | 5.200 | 5.580 | 5.191 | −0.009 | 5.563 | −0.017 | 1652225 | (1.376%) |
| 34 | i-Paraffins | 43 | 57 | 71 | 85 | 99 | 113 | | | 5.580 | 6.153 | 5.563 | −0.017 | 6.149 | −0.004 | 2464586 | (2.053%) |
| 35 | Cyclopara. | 41 | 55 | 69 | 83 | 97 | 111 | | | 5.580 | 6.153 | 5.563 | −0.017 | 6.149 | −0.004 | 3570701 | (2.974%) |
| 36 | CnH2n-8 | 117 | 131 | 145 | 159 | 163 | 177 | | | 5.580 | 6.153 | 5.563 | −0.017 | 6.149 | −0.004 | 1070407 | (0.892%) |
| 37 | CnH2n-6 | 91 | 105 | 119 | 133 | 147 | 161 | | | 5.580 | 6.153 | 5.563 | −0.017 | 6.149 | −0.004 | 4083260 | (3.401%) |
| 38 | CnH2n-12 | 141 | 155 | 169 | 183 | 197 | 211 | | | 5.580 | 6.153 | 5.563 | −0.017 | 6.149 | −0.004 | 53301 | (0.044%) |
| 39 | CnH2n-10 | 115 | 129 | 143 | 157 | 171 | 185 | | | 5.580 | 6.153 | 5.563 | −0.017 | 6.149 | −0.004 | 513956 | (0.428%) |
| 40 | CnH2n-18 | 178 | 191 | 205 | 219 | 233 | 247 | | | 5.580 | 6.153 | 5.563 | −0.017 | 6.149 | −0.004 | 0 | (0.000%) |
| 41 | n-C12 | 43 | 57 | 71 | 85 | 99 | 170 | | | 6.153 | 6.178 | 6.149 | −0.004 | 6.175 | −0.004 | 102837 | (0.086%) |
| 42 | i-Paraffins | 43 | 57 | 71 | 85 | 99 | 113 | | | 6.178 | 6.635 | 6.175 | −0.003 | 6.642 | 0.007 | 2177892 | (1.814%) |
| 43 | Cyclopara. | 41 | 55 | 69 | 83 | 97 | 111 | | | 6.178 | 6.635 | 6.175 | −0.003 | 6.642 | 0.007 | 3170290 | (2.640%) |

-continued

COMPLETE CHEMIST'S RULES FOR DISTILLATES WITH CORRECTIONS

Total Raw Abundance (TIC): 264722694
Chemist Rule: 120067945 (45.356%)
Air Leakage: 251310 (0.095%)
Avg Scan Rate (Min/Max): 215 (215/216)
Number of Records: 4168

| Rule[a] | Compound[b] | Masses[c] | | | | | | | | Start[d] | End[e] | CStart[f] | Corr[g] | CEnd[h] | Corr[j] | Abundance[i] |
|---|---|---|---|---|---|---|---|---|---|---|---|---|---|---|---|---|
| 44 | CnH2n-8 | 117 | 131 | 145 | 159 | 163 | 177 | | | 6.178 | 6.635 | 6.175 | -0.003 | 6.642 | 0.007 | 2141612 (1.784%) |
| 45 | CnH2n-6 | 91 | 105 | 119 | 133 | 147 | 161 | | | 6.178 | 6.635 | 6.175 | -0.003 | 6.642 | 0.007 | 2762976 (2.301%) |
| 46 | CnH2n-12 | 141 | 155 | 169 | 183 | 197 | 211 | | | 6.178 | 6.635 | 6.175 | -0.003 | 6.642 | 0.007 | 101796 (0.085%) |
| 47 | CnH2n-10 | 115 | 129 | 143 | 157 | 171 | 185 | | | 6.178 | 6.635 | 6.175 | -0.003 | 6.642 | 0.007 | 808048 (0.673%) |
| 48 | CnH2n-18 | 178 | 191 | 205 | 219 | 233 | 247 | | | 6.178 | 6.635 | 6.175 | -0.003 | 6.642 | 0.007 | 1665 (0.001%) |
| 49 | n-C13 | 43 | 57 | 71 | 85 | 99 | 184 | | | 6.635 | 6.692 | 6.642 | 0.007 | 6.700 | 0.008 | 911705 (0.759%) |
| 50 | i-Paraffins | 43 | 57 | 71 | 85 | 99 | 113 | | | 6.692 | 7.124 | 6.700 | 0.008 | 7.133 | 0.009 | 2349382 (1.957%) |
| 51 | Cyclopara. | 41 | 55 | 69 | 83 | 97 | 111 | | | 6.692 | 7.124 | 6.700 | 0.008 | 7.133 | 0.009 | 3248819 (2.705%) |
| 52 | CnH2n-8 | 117 | 131 | 145 | 159 | 163 | 177 | | | 6.692 | 7.124 | 6.700 | 0.008 | 7.133 | 0.009 | 3468731 (2.889%) |
| 53 | CnH2n-6 | 91 | 105 | 119 | 133 | 147 | 161 | | | 6.692 | 7.124 | 6.700 | 0.008 | 7.133 | 0.009 | 2383596 (1.985%) |
| 54 | CnH2n-12 | 141 | 155 | 169 | 183 | 197 | 211 | | | 6.692 | 7.124 | 6.700 | 0.008 | 7.133 | 0.009 | 1725420 (1.437%) |
| 55 | CnH2n-10 | 115 | 129 | 143 | 157 | 171 | 185 | | | 6.692 | 7.124 | 6.700 | 0.008 | 7.133 | 0.009 | 1994509 (1.661%) |
| 56 | CnH2n-18 | 178 | 191 | 205 | 219 | 233 | 247 | | | 6.692 | 7.124 | 6.700 | 0.008 | 7.133 | 0.009 | 13935 (0.012%) |
| 57 | n-C14 | 43 | 57 | 71 | 85 | 99 | 198 | | | 7.124 | 7.184 | 7.133 | 0.009 | 7.193 | 0.009 | 1111453 (0.926%) |
| 58 | i-Paraffins | 43 | 57 | 71 | 85 | 99 | 113 | | | 7.124 | 7.593 | 7.133 | 0.009 | 7.602 | 0.009 | 3370658 (2.807%) |
| 59 | Cyclopara. | 41 | 55 | 69 | 83 | 97 | 111 | | | 7.124 | 7.593 | 7.133 | 0.009 | 7.602 | 0.009 | 3986691 (3.320%) |
| 60 | CnH2n-8 | 117 | 131 | 145 | 159 | 163 | 177 | | | 7.124 | 7.593 | 7.133 | 0.009 | 7.602 | 0.009 | 817090 (2.380%) |
| 61 | CnH2n-6 | 91 | 105 | 119 | 133 | 147 | 161 | | | 7.124 | 7.593 | 7.133 | 0.009 | 7.602 | 0.009 | 1811945 (1.509%) |
| 62 | CnH2n-12 | 141 | 155 | 169 | 183 | 197 | 211 | | | 7.124 | 7.593 | 7.133 | 0.009 | 7.602 | 0.009 | 29798051 (2.482%) |
| 63 | CnH2n-10 | 115 | 129 | 143 | 157 | 171 | 185 | | | 7.124 | 7.593 | 7.133 | 0.009 | 7.602 | 0.009 | 2321206 (1.933%) |
| 64 | CnH2n-18 | 178 | 191 | 205 | 219 | 233 | 247 | | | 7.124 | 7.593 | 7.133 | 0.009 | 7.602 | 0.009 | 20724 (0.017%) |
| 65 | n-C15 | 43 | 57 | 71 | 85 | 99 | 212 | | | 7.593 | 7.645 | 7.602 | 0.009 | 7.654 | 0.009 | 1011272 (0.842%) |
| 66 | i-Paraffins | 43 | 57 | 71 | 85 | 99 | 113 | | | 7.645 | 8.016 | 7.654 | 0.009 | 8.026 | 0.010 | 1865267 (1.554%) |
| 67 | Cyclopara. | 41 | 55 | 69 | 83 | 97 | 111 | | | 7.645 | 8.016 | 7.654 | 0.009 | 8.026 | 0.010 | 2680266 (2.232%) |
| 68 | CnH2n-8 | 117 | 131 | 145 | 159 | 163 | 177 | | | 7.645 | 8.016 | 7.654 | 0.009 | 8.026 | 0.010 | 1237345 (1.031%) |
| 69 | CnH2n-6 | 91 | 105 | 119 | 133 | 147 | 161 | | | 7.645 | 8.016 | 7.654 | 0.009 | 8.026 | 0.010 | 1171815 (0.976%) |
| 70 | CnH2n-12 | 141 | 155 | 169 | 183 | 197 | 211 | | | 7.645 | 8.016 | 7.654 | 0.009 | 8.026 | 0.010 | 31139981 (2.594%) |
| 71 | CnH2n-10 | 115 | 129 | 143 | 157 | 171 | 185 | | | 7.645 | 8.016 | 7.654 | 0.009 | 8.026 | 0.010 | 1671775 (1.392%) |
| 72 | CnH2n-18 | 178 | 191 | 205 | 219 | 233 | 247 | | | 7.645 | 8.016 | 7.654 | 0.009 | 8.026 | 0.010 | 11492 (0.010%) |
| 73 | n-C16 | 43 | 57 | 71 | 85 | 99 | 226 | | | 8.079 | 8.079 | 8.026 | 0.009 | 8.089 | 0.010 | 881371 (0.734%) |
| 74 | i-Paraffins | 43 | 57 | 71 | 85 | 99 | 113 | | | 8.079 | 8.430 | 8.089 | 0.010 | 8.438 | 0.008 | 1784488 (1.486%) |
| 75 | Cyclopara. | 41 | 55 | 69 | 83 | 97 | 111 | | | 8.079 | 8.430 | 8.089 | 0.010 | 8.438 | 0.008 | 2478286 (2.064%) |
| 76 | CnH2n-8 | 117 | 131 | 145 | 159 | 163 | 177 | | | 8.079 | 8.430 | 8.089 | 0.010 | 8.438 | 0.008 | 740960 (0.617%) |
| 77 | CnH2n-6 | 91 | 105 | 119 | 133 | 147 | 161 | | | 8.079 | 8.430 | 8.089 | 0.010 | 8.438 | 0.008 | 8904331 (0.742%) |
| 78 | CnH2n-12 | 141 | 155 | 169 | 183 | 197 | 211 | | | 8.079 | 8.430 | 8.089 | 0.010 | 8.438 | 0.008 | 2293832 (1.910%) |
| 79 | CnH2n-10 | 115 | 129 | 143 | 157 | 171 | 185 | | | 8.079 | 8.430 | 8.089 | 0.010 | 8.438 | 0.008 | 1338765 (1.115%) |
| 80 | CnH2n-18 | 178 | 191 | 205 | 219 | 233 | 247 | | | 8.079 | 8.430 | 8.089 | 0.010 | 8.438 | 0.008 | 73336 (0.061%) |
| 81 | n-C17 | 43 | 57 | 71 | 85 | 99 | 240 | | | 8.476 | 8.476 | 8.484 | 0.008 | 8.484 | 0.008 | 826222 (0.688%) |
| 82 | i-Paraffins | 43 | 57 | 71 | 85 | 99 | 113 | | | 8.476 | 8.808 | 8.484 | 0.008 | 8.814 | 0.006 | 1639560 (1.366%) |
| 83 | Cyclopara. | 41 | 55 | 69 | 83 | 97 | 111 | | | 8.476 | 8.808 | 8.484 | 0.008 | 8.814 | 0.006 | 2111240 (1.758%) |
| 84 | CnH2n-8 | 117 | 131 | 145 | 159 | 163 | 177 | | | 8.476 | 8.808 | 8.484 | 0.008 | 8.814 | 0.006 | 4777911 (0.398%) |
| 85 | CnH2n-6 | 91 | 105 | 119 | 133 | 147 | 161 | | | 8.476 | 8.808 | 8.484 | 0.008 | 8.814 | 0.006 | 6158121 (0.513%) |
| 86 | CnH2n-12 | 141 | 155 | 169 | 183 | 197 | 211 | | | 8.476 | 8.808 | 8.484 | 0.008 | 8.814 | 0.006 | 1564845 (1.303%) |
| 87 | CnH2n-10 | 115 | 129 | 143 | 157 | 171 | 185 | | | 8.476 | 8.808 | 8.484 | 0.008 | 8.814 | 0.006 | 854998 (0.712%) |

5,602,755

COMPLETE CHEMIST'S RULES FOR DISTILLATES WITH CORRECTIONS —continued

Total Raw Abundance (TIC): 264722694
Chemist Rule: 120067945 (45.356%)
Air Leakage: 251310 (0.095%)
Avg Scan Rate (Min/Max): 215 (215/216)
Number of Records: 4168

| Rule[a] | Compound[b] | | | Masses[e] | | | | | | Start[d] | End[c] | CStart[f] | CEnd[h] | Corr[g] | Corr[j] | Abundance[i] |
|---|---|---|---|---|---|---|---|---|---|---|---|---|---|---|---|---|
| 88 | CnH2n-18 | 178 | 191 | 205 | 219 | 233 | 247 | 8.476 | 8.808 | 8.484 | 8.814 | 0.008 | 0.006 | 243918 (0.203%) |
| 89 | n-C18 | 43 | 57 | 71 | 85 | 99 | 254 | 8.808 | 8.866 | 8.814 | 8.872 | 0.006 | 0.006 | 668888 (0.557%) |
| 90 | i-Paraffins | 43 | 57 | 71 | 85 | 99 | 113 | 8.866 | 9.187 | 8.872 | 9.192 | 0.006 | 0.005 | 1319602 (1.099%) |
| 91 | Cyclopara. | 41 | 55 | 69 | 83 | 97 | 111 | 8.866 | 9.187 | 8.872 | 9.192 | 0.006 | 0.005 | 1693248 (1.410%) |
| 92 | CnH2n-8 | 117 | 131 | 145 | 159 | 163 | 177 | 8.866 | 9.187 | 8.872 | 9.192 | 0.006 | 0.005 | 327028 (0.272%) |
| 93 | CnH2n-6 | 91 | 105 | 119 | 133 | 147 | 161 | 8.866 | 9.187 | 8.872 | 9.192 | 0.006 | 0.005 | 454840 (0.379%) |
| 94 | CnH2n-12 | 141 | 155 | 169 | 183 | 197 | 211 | 8.866 | 9.187 | 8.872 | 9.192 | 0.006 | 0.005 | 781816 (0.651%) |
| 95 | CnH2n-10 | 115 | 129 | 143 | 157 | 171 | 185 | 8.866 | 9.187 | 8.872 | 9.192 | 0.006 | 0.005 | 451709 (0.376%) |
| 96 | CnH2n-18 | 178 | 191 | 205 | 219 | 233 | 247 | 8.866 | 9.187 | 8.872 | 9.192 | 0.006 | 0.005 | 707048 (0.589%) |
| 97 | n-C19 | 43 | 57 | 71 | 85 | 99 | 268 | 9.187 | 9.234 | 9.192 | 9.239 | 0.005 | 0.005 | 472812 (0.394%) |
| 98 | i-Paraffins | 43 | 57 | 71 | 85 | 99 | 113 | 9.234 | 9.523 | 9.239 | 9.527 | 0.005 | 0.004 | 846072 (0.705%) |
| 99 | Cyclopara. | 41 | 55 | 69 | 83 | 97 | 111 | 9.234 | 9.523 | 9.239 | 9.527 | 0.005 | 0.004 | 1183659 (0.986%) |
| 100 | CnH2n-8 | 117 | 131 | 145 | 159 | 163 | 177 | 9.234 | 9.523 | 9.239 | 9.527 | 0.005 | 0.004 | 200520 (0.167%) |
| 101 | CnH2n-6 | 91 | 105 | 119 | 133 | 147 | 161 | 9.234 | 9.523 | 9.239 | 9.527 | 0.005 | 0.004 | 287782 (0.240%) |
| 102 | CnH2n-12 | 141 | 155 | 169 | 183 | 197 | 211 | 9.234 | 9.523 | 9.239 | 9.527 | 0.005 | 0.004 | 623931 (0.520%) |
| 103 | CnH2n-10 | 115 | 129 | 143 | 157 | 171 | 185 | 9.234 | 9.523 | 9.239 | 9.527 | 0.005 | 0.004 | 239295 (0.199%) |
| 104 | CnH2n-18 | 178 | 191 | 205 | 219 | 233 | 247 | 9.234 | 9.523 | 9.239 | 9.527 | 0.005 | 0.004 | 741840 (0.618%) |
| 105 | n-C20 | 43 | 57 | 71 | 85 | 99 | 282 | 9.523 | 9.578 | 9.527 | 9.582 | 0.005 | 0.004 | 333899 (0.278%) |
| 106 | i-Paraffins | 43 | 57 | 71 | 85 | 99 | 113 | 9.578 | 9.860 | 9.582 | 9.864 | 0.004 | 0.004 | 550035 (0.458%) |
| 107 | Cyclopara. | 41 | 55 | 69 | 83 | 97 | 111 | 9.578 | 9.860 | 9.582 | 9.864 | 0.004 | 0.004 | 752095 (0.626%) |
| 108 | CnH2n-8 | 117 | 131 | 145 | 159 | 163 | 177 | 9.578 | 9.860 | 9.582 | 9.864 | 0.004 | 0.004 | 63033 (0.052%) |
| 109 | CnH2n-6 | 91 | 105 | 119 | 133 | 147 | 161 | 9.578 | 9.860 | 9.582 | 9.864 | 0.004 | 0.004 | 188706 (0.157%) |
| 110 | CnH2n-12 | 141 | 155 | 169 | 183 | 197 | 211 | 9.578 | 9.860 | 9.582 | 9.864 | 0.004 | 0.004 | 479998 (0.400%) |
| 111 | CnH2n-10 | 115 | 129 | 143 | 157 | 171 | 185 | 9.578 | 9.860 | 9.582 | 9.864 | 0.004 | 0.004 | 94768 (0.079%) |
| 112 | CnH2n-18 | 178 | 191 | 205 | 219 | 233 | 247 | 9.578 | 9.860 | 9.582 | 9.864 | 0.004 | 0.004 | 4559521 (0.380%) |
| 113 | n-C21 | 43 | 57 | 71 | 85 | 99 | 296 | 9.860 | 9.912 | 9.864 | 9.916 | 0.004 | 0.004 | 224895 (0.187%) |
| 114 | i-Paraffins | 43 | 57 | 71 | 85 | 99 | 113 | 9.912 | 10.163 | 9.916 | 10.167 | 0.004 | 0.004 | 337240 (0.281%) |
| 115 | Cyclopara. | 41 | 55 | 69 | 83 | 93 | 111 | 9.912 | 10.163 | 9.916 | 10.167 | 0.004 | 0.004 | 459847 (0.383%) |
| 116 | CnH2n-8 | 117 | 131 | 145 | 159 | 163 | 177 | 9.912 | 10.163 | 9.916 | 10.167 | 0.004 | 0.004 | 40739 (0.034%) |
| 117 | CnH2n-6 | 91 | 105 | 119 | 133 | 147 | 161 | 9.912 | 10.163 | 9.916 | 10.167 | 0.004 | 0.004 | 62686 (0.052%) |
| 118 | CnH2n-12 | 141 | 155 | 169 | 183 | 197 | 211 | 9.912 | 10.163 | 9.916 | 10.167 | 0.004 | 0.004 | 187479 (0.156%) |
| 119 | CnH2n-10 | 115 | 129 | 143 | 157 | 171 | 185 | 9.912 | 10.163 | 9.916 | 10.167 | 0.004 | 0.004 | 33918 (0.028%) |
| 120 | CnH2n-18 | 178 | 191 | 205 | 219 | 233 | 247 | 9.912 | 10.163 | 9.916 | 10.167 | 0.004 | 0.004 | 482808 (0.402%) |
| 121 | n-C22 | 43 | 57 | 71 | 85 | 99 | 310 | 10.163 | 10.266 | 10.167 | 10.270 | 0.004 | 0.004 | 169840 (0.141%) |
| 122 | i-Paraffins | 43 | 57 | 71 | 85 | 99 | 113 | 10.266 | 10.519 | 10.270 | 10.523 | 0.004 | 0.004 | 148458 (0.124%) |
| 123 | Cyclopara. | 41 | 55 | 69 | 83 | 93 | 111 | 10.266 | 10.519 | 10.270 | 10.523 | 0.004 | 0.004 | 231145 (0.193%) |
| 124 | CnH2n-8 | 117 | 131 | 145 | 159 | 163 | 177 | 10.266 | 10.519 | 10.270 | 10.523 | 0.004 | 0.004 | 5987 (0.005%) |
| 125 | CnH2n-6 | 91 | 105 | 119 | 133 | 147 | 161 | 10.266 | 10.519 | 10.270 | 10.523 | 0.004 | 0.004 | 8802 (0.007%) |
| 126 | CnH2n-12 | 141 | 155 | 169 | 183 | 197 | 211 | 10.266 | 10.519 | 10.270 | 10.523 | 0.004 | 0.004 | 25518 (0.021%) |
| 127 | CnH2n-10 | 115 | 129 | 143 | 157 | 171 | 185 | 10.266 | 10.519 | 10.270 | 10.523 | 0.004 | 0.004 | 2125 (0.002%) |
| 128 | CnH2n-18 | 178 | 191 | 205 | 219 | 233 | 247 | 10.266 | 10.519 | 10.270 | 10.523 | 0.004 | 0.004 | 273607 (0.228%) |
| 129 | n-C23 | 43 | 57 | 71 | 85 | 99 | 324 | 10.519 | 10.619 | 10.523 | 10.623 | 0.004 | 0.004 | 83101 (0.069%) |
| 130 | i-Paraffins | 43 | 57 | 71 | 85 | 99 | 113 | 10.619 | 10.912 | 10.623 | 10.916 | 0.004 | 0.004 | 43464 (0.036%) |
| 131 | Cyclopara. | 41 | 55 | 69 | 83 | 97 | 111 | 10.619 | 10.912 | 10.623 | 10.916 | 0.004 | 0.004 | 38319 (0.032%) |

-continued

COMPLETE CHEMIST'S RULES FOR DISTILLATES WITH CORRECTIONS

Total Raw Abundance (TIC): 264722694
Chemist Rule: 120067945 (45.356%)
Air Leakage: 251310 (0.095%)
Avg Scan Rate (Min/Max): 215 (215/216)
Number of Records: 4168

| Rule[a] | Compound[b] | Masses[c] | | | | | | | Start[d] | End[e] | CStart[f] | CEnd[h] | Corr[g] | Corr[i] | Abundance[j] |
|---|---|---|---|---|---|---|---|---|---|---|---|---|---|---|---|
| 132 | CnH2n-8 | 117 | 131 | 145 | 159 | 163 | 177 | | 10.619 | 10.912 | 10.623 | 10.916 | 0.004 | 0.004 | 0 (0.000%) |
| 133 | CnH2n-6 | 91 | 105 | 119 | 133 | 147 | 161 | | 10.619 | 10.912 | 10.623 | 10.916 | 0.004 | 0.004 | 0 (0.000%) |
| 134 | CnH2n-12 | 141 | 155 | 169 | 183 | 197 | 211 | | 10.619 | 10.912 | 10.623 | 10.916 | 0.004 | 0.004 | 0 (0.000%) |
| 135 | CnH2n-10 | 115 | 129 | 143 | 157 | 171 | 185 | | 10.619 | 10.912 | 10.623 | 10.916 | 0.004 | 0.004 | 0 (0.000%) |
| 136 | CnH2n-18 | 178 | 191 | 205 | 219 | 233 | 247 | | 10.619 | 10.912 | 10.623 | 10.916 | 0.004 | 0.004 | 47617 (0.040%) |
| 137 | n-C24 | 43 | 57 | 71 | 85 | 99 | 338 | | 10.912 | 10.964 | 10.916 | 10.968 | 0.004 | 0.004 | 21521 (0.018%) |
| 138 | i-Paraffins | 43 | 57 | 71 | 85 | 99 | 113 | | 10.964 | 14.800 | 10.968 | 14.804 | 0.004 | 0.004 | 10799 (0.009%) |
| 139 | Cyclopara. | 41 | 55 | 69 | 83 | 97 | 111 | | 10.964 | 14.800 | 10.968 | 14.804 | 0.004 | 0.004 | 2092 (0.002%) |
| 140 | CnH2n-8 | 117 | 131 | 145 | 159 | 163 | 177 | | 10.964 | 14.800 | 10.968 | 14.804 | 0.004 | 0.004 | 0 (0.000%) |
| 141 | CnH2n-6 | 91 | 105 | 119 | 133 | 147 | 161 | | 10.964 | 14.800 | 10.968 | 14.904 | 0.004 | 0.004 | 0 (0.000%) |
| 142 | nH2n-12 | 141 | 155 | 169 | 183 | 197 | 211 | | 10.964 | 14.800 | 10.968 | 14.804 | 0.004 | 0.004 | 0 (0.000%) |
| 143 | CnH2n-10 | 115 | 129 | 143 | 157 | 171 | 185 | | 10.964 | 14.800 | 10.968 | 14.804 | 0.004 | 0.004 | 0 (0.000%) |
| 144 | CnH2n-18 | 178 | 191 | 205 | 219 | 233 | 247 | | 10.964 | 14.800 | 10.968 | 14.804 | 0.004 | 0.004 | 0 (0.000%) |

Sum = ++++++++++++ ++++++++++ 120067945 (100.000%)

[a] Rule number, integer index
[b] Compound or group of compounds rules applies to:
cyclopara's alkylated 1 ring cycloparaffins
$C_nH_{2n-6}$ alkylated benzenes
$C_nH_{2n-8}$ alkylated indanes
$C_nH_{2n-10}$ alkylated indenes
$C_nH_{2n-12}$ alkylated naphthalenes
$C_nH_{2n-18}$ alkylated phenanthrenes/anthracenes
[c] Masses used in Rule [up to n may be specified, where n is an integer which is equal to the number of masses scanned during the time interval ([d] to [e]) either in full scan mode or selected ion monitoring mode].
[d] Start retention time in minutes
[e] end retention time in minutes
[f] corrected start retention time
[g] correction = difference between start and cstart (in minutes)
[h] corrected end retention time
[i] correction = difference between end and cend (in minutes)
[j] Abundance, both as total sum and as normalized percentage based on Chemist's Rules.

What is claimed is:

1. A method for predicting physical, perceptual, performance or chemical properties of a complex hydrocarbon mixture which comprises:

(a) selecting at least one property of the hydrocarbon mixture;

(b) selecting reference samples, said reference samples containing characteristic compound types present in the complex hydrocarbon mixture and which have known values of the property or properties selected in step (a);

(c) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each reference sample into the mass spectrometer, under dynamic flow conditions;

(3) obtaining for each reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of characteristic compounds or molecular classes expected within the retention time window;

(7) recording the total amount of each characteristic compound or compound group selected in step c(6);

(8) forming the data from steps c(6) and c(7) into a X-block matrix;

(9) forming the data selected in (a) for reference samples selected in (b) into a Y-block matrix;

(10) analyzing the data from steps c(8) and c(9) by multivariate correlation techniques including Partial Least Squares, Principal Component Regression, or Ridge Regression to produce a series of coefficients;

(d) subjecting an unknown hydrocarbon mixture to steps c(1) to c(3) in the same manner as the reference sample to produce a series of time resolved mass chromatograms;

(e) repeating steps c(4) to c(8) for each mass chromatogram from step (d);

(f) multiplying the matrix from step (e) by the coefficients from step c(10) to produce a predicted value of the property or properties.

2. The method of claim 1 wherein the gas chromatograph is a capillary gas chromatograph and the mass spectrometer is a quadrupole mass spectrometer.

3. The method of claim 1 wherein the gas chromatograph and mass spectrometer are operated under repeatable conditions.

4. The method of claim 1 wherein the selection of a series of molecular and/or fragment ions characteristic of compounds or compound classes is accomplished using Chemist's Rules.

5. The method of claim 1 wherein the selection of a series of molecular and/or fragment ions characteristic of compounds or compound classes is accomplished using Hydrocarbon Type Analysis.

6. The method of claim 1 wherein data from the gas chromatograph and mass spectrometer are stored in a computer.

7. The method of claim 1 wherein data from steps (c) to (f) are treated in a computer.

8. The method of claim 1 wherein other chemical, performance, perceptual or physical properties of the hydrocarbon mixture are selected.

9. The method of claim 1 wherein the data are collinear.

10. The method of claim 1 wherein the multivariate correlation technique is Partial Least Squares.

* * * * *